(12) United States Patent
Kawano

(10) Patent No.: US 8,186,305 B2
(45) Date of Patent: May 29, 2012

(54) IN-VIVO EXAMINATION APPARATUS

(75) Inventor: Yoshihiro Kawano, Fuchu (JP)

(73) Assignee: Olympus Corporation, Tokyo (JP)

(*) Notice: Subject to any disclaimer, the term of this patent is extended or adjusted under 35 U.S.C. 154(b) by 610 days.

(21) Appl. No.: 12/308,797

(22) PCT Filed: Jun. 27, 2007

(86) PCT No.: PCT/JP2007/062880
§ 371 (c)(1),
(2), (4) Date: Dec. 23, 2008

(87) PCT Pub. No.: WO2008/004474
PCT Pub. Date: Jan. 10, 2008

(65) Prior Publication Data
US 2009/0301401 A1    Dec. 10, 2009

(30) Foreign Application Priority Data
Jul. 6, 2006   (JP) .................................. 2006-186604

(51) Int. Cl.
*A01K 29/00*   (2006.01)
(52) U.S. Cl. ........................................................ 119/420
(58) Field of Classification Search .................. 119/420, 119/421, 416, 417, 418; 128/203.12
See application file for complete search history.

(56) References Cited

U.S. PATENT DOCUMENTS

| | | | |
|---|---|---|---|
| 3,557,785 A * | 1/1971 | McQueen ................. 128/205.16 |
| 3,897,751 A * | 8/1975 | Gullino et al. ................. 119/420 |
| 4,252,080 A * | 2/1981 | Gioia et al. ..................... 119/6.5 |
| 4,582,055 A * | 4/1986 | McDougal et al. ....... 128/202.12 |
| 4,787,382 A * | 11/1988 | Pekovic .................... 128/203.25 |
| 4,941,431 A * | 7/1990 | Anderson et al. .............. 119/420 |
| 5,220,882 A * | 6/1993 | Jenkins ......................... 119/420 |
| 6,352,076 B1 | 3/2002 | Frenchw |
| 6,776,158 B1 * | 8/2004 | Anderson et al. ........ 128/203.12 |
| 7,252,050 B2 * | 8/2007 | Cole ............................. 119/416 |
| 7,331,341 B2 * | 2/2008 | Nelson .................... 128/203.12 |
| 7,341,023 B2 * | 3/2008 | Caplette ........................ 119/420 |
| 7,438,021 B2 * | 10/2008 | Dietrich ........................ 119/420 |
| 7,464,707 B2 * | 12/2008 | Dalgetty et al. .......... 128/203.15 |
| 7,503,323 B2 * | 3/2009 | Dalgetty et al. .......... 128/203.15 |
| 7,533,702 B2 * | 5/2009 | Barre .............................. 141/66 |
| 2003/0154976 A1 * | 8/2003 | Dalgetty et al. .......... 128/203.14 |
| 2004/0216737 A1 | 11/2004 | Anderson |
| 2006/0011143 A1 * | 1/2006 | Drummond et al. ........... 119/420 |
| 2009/0151720 A1 * | 6/2009 | Inoue et al. ............... 128/203.12 |
| 2009/0223460 A1 * | 9/2009 | Starr et al. ..................... 119/420 |

FOREIGN PATENT DOCUMENTS

JP    02-177955    7/1990

OTHER PUBLICATIONS

International Search Report dated Jul. 24, 2007, PCT International Appln. No. PCT/JP2007/062880 filed Jun. 27, 2007.

* cited by examiner

*Primary Examiner* — Yvonne Abbott
(74) *Attorney, Agent, or Firm* — Kenyon & Kenyon LLP

(57) ABSTRACT

The present invention prevents the leakage of anesthetic gas, and enables in vivo observation of a specimen such as small laboratory animals over a long period of time. An in-vivo examination apparatus (1) comprises: a stage (2) for mounting a specimen (A) such as a laboratory animal; an anesthetizing chamber (3) which is disposed on the stage (2) for housing the specimen (A); and an anesthetic gas supply device (4) for supplying anesthetic gas (G) into the anesthetizing chamber (3); wherein a transparent window (3c) is provided on at least a part of the anesthetizing chamber (3).

2 Claims, 5 Drawing Sheets

IN-VIVO EXAMINATION APPARATUS

TECHNICAL FIELD

This invention relates to an in-vivo examination apparatus for observation of a specimen such as a small laboratory animal in vivo.

BACKGROUND ART

Inhalant anesthesia machines for use with small laboratory animals have been developed in order to maintain the animal in a live state without causing pain when performing in vivo observation of a specimen such as the small laboratory animal. In these inhalant anesthesia machines, the nose and mouth of the mouse is covered with a bag-like inhalation device, and the small laboratory animal is placed in a somnolent, or anesthetized, state by supplying anesthetic gas into the inhalation device.

Non-patent Document 1:
S.A. Techno K.K., Yuzuru KURABAYASHI, Research Related to the Development of Inhalant Anesthesia Apparatuses for Small Laboratory Animals, [online], Okayama University, [searched on Jun. 7, 1995], Internet <URL: http://www.chugoku.meti.go.jp/topics/sangakukan/jirei/2-11.pdf>

DISCLOSURE OF INVENTION

However, in such conventional inhalant anesthesia machines, it is difficult to achieve a complete seal of the space that is formed between the inhalant device and the small laboratory animal's nose and mouth. As a result, when observations are carried out over a long period of time while maintaining the animal in an anesthetized state, an undesirable situation results in which anesthetic gas leaks from this space.

The present invention was conceived in view of the above-described circumstances with an object of providing an in-vivo examination apparatus in which the leakage of anesthetic gas is prevented, and with which it is possible to observe a specimen such as a small laboratory animal in vivo over a long period of time.

In order to achieve the above object, the present invention offers the following solutions.

The present invention provides an in-vivo examination apparatus comprising: a stage for mounting a specimen such as a laboratory animal; an anesthetizing chamber which is disposed on the stage for housing the specimen; and an anesthetic gas supply device for supplying anesthetic gas into the anesthetizing chamber; wherein a transparent window is provided on at least a part of the anesthetizing chamber.

In an aspect of the present invention, a specimen such as a laboratory animal is housed inside the anesthetizing chamber, and anesthetic gas is supplied into a chamber main body by the operation of the anesthetic gas supply device; as a result of which, the specimen can be maintained in an anesthetized state. Since a transparent window is provided on the chamber main body, it is possible to observe the specimen through this window in an optical manner. In this case, since the specimen is housed in the anesthetizing chamber, it is possible to prevent leakage of the anesthetic gas into the surrounding environment, and to maintain the specimen in an anesthetized state over a relatively long period of time.

In this aspect, the configuration may also be such that the anesthetizing chamber is detachably provided on the stage, and there is provided a connecting mechanism for connecting the anesthetic gas supply device and the anesthetizing chamber when the anesthetizing chamber is attached to the stage.

By so doing, the anesthetizing chamber can be detached from the stage, and the specimen can be transferred into the anesthetizing chamber in a wider environment. As a result, the workability can be improved. When the anesthetizing chamber is attached to the stage, the anesthetic gas supply device is connected to the anesthetizing chamber by the operation of the connecting mechanism. Therefore, there is no need of taking the specimen out from the anesthetizing chamber, but the specimen can be directly maintained in an anesthetized state by the operation of the anesthetic gas supply device, so that in vivo observation can be performed.

Moreover, in this aspect, the stage may also be provided with a positioning device for fixing the anesthetizing chamber in a positioned state.

By so doing, the positional relation between the stage and the anesthetizing chamber can be coordinated, so that microscopic observation can be readily performed in an observable range within the anesthetizing chamber by movement of the stage.

Furthermore, in this aspect, there may also be provided: a sensor for detecting the attachment/detachment of the anesthetizing chamber to/from the stage; and a control unit for operating the anesthetic gas supply device on the basis of a detection signal from the sensor which indicates the attachment of the anesthetizing chamber to the stage.

By so doing, the anesthetic gas supply device can be automatically operated at the time of the attachment of the anesthetizing chamber, so that the operation for anesthetizing the specimen can be facilitated. Moreover, when the anesthetizing chamber is detached from the stage, the operation of the anesthetic gas supply device can be stopped so that the leakage of the anesthetic gas into the surrounding environment can be prevented.

The present invention provides the effect of preventing the leakage of anesthetic gas, and enabling in vivo observation of a specimen such as a small laboratory animal over a long period of time.

EXPLANATION OF REFERENCE SIGNS

Figure 1:
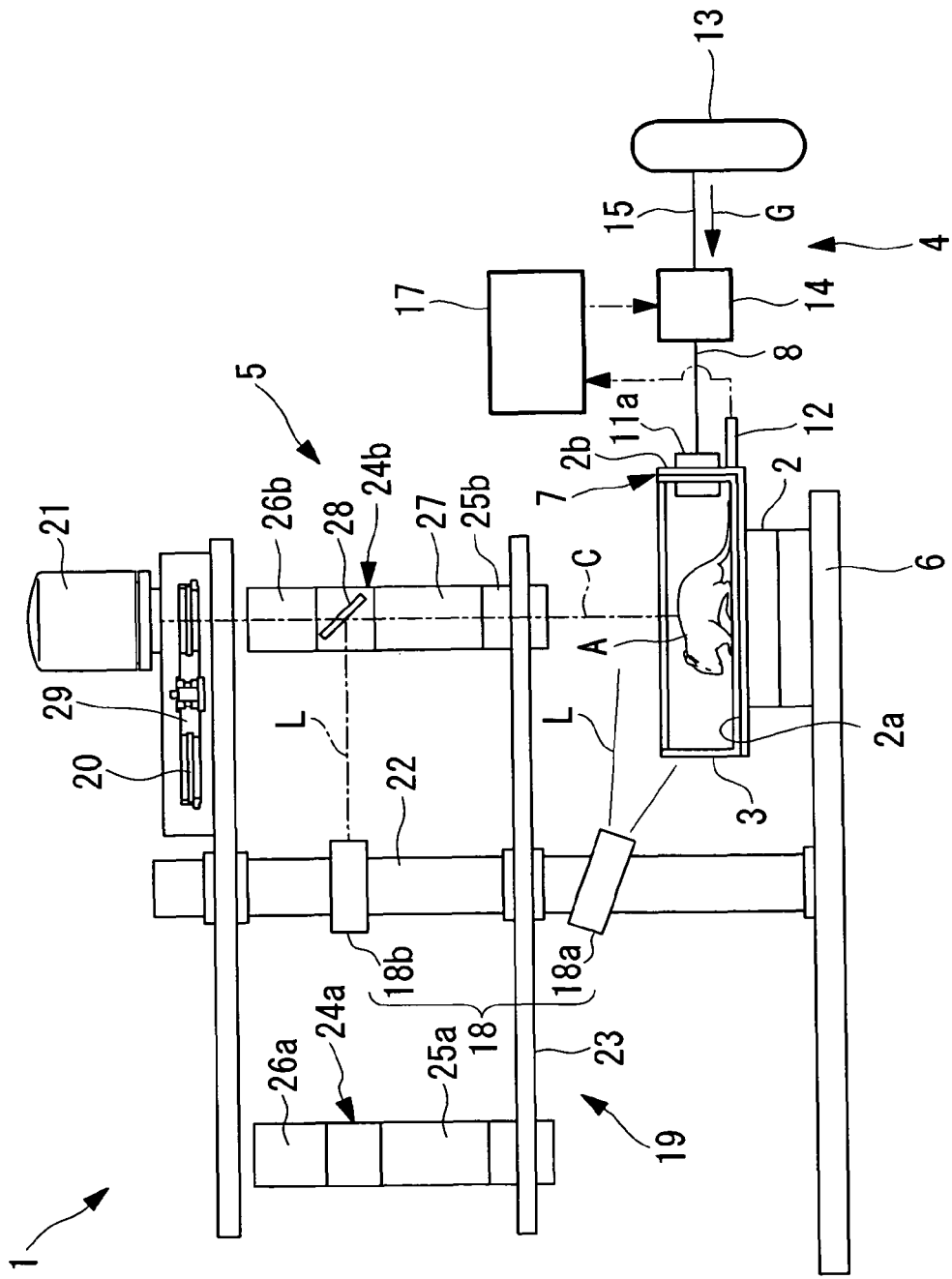
FIG. 1 is an overall block diagram showing the in-vivo examination apparatus according to an embodiment of the present invention.

G: anesthetic gas
1: In-vivo examination apparatus
2: stage
3: anesthetizing chamber
3c: lid member (Window)
4: anesthetic gas supply device
7: positioning mechanism (Positioning device)
11a, 11b, 16a, 16b: connector (Connecting mechanism)
12: sensor
14: vaporizer (Anesthetic gas supply device)
17: control unit

BEST MODE FOR CARRYING OUT THE INVENTION

The in-vivo examination apparatus 1 according to one embodiment of the present invention will now be explained with reference to FIG. 1 to FIG. 4C.

As shown in FIG. 1, the in-vivo examination apparatus according to this embodiment comprises: a stage 2 for mounting a specimen A; an anesthetizing chamber 3 that is detachably attached to the stage 2; an anesthetic gas supply device 4 connected to the anesthetizing chamber 3; and an observation optical system 5 for observing the specimen A inside the anesthetizing chamber 3 that is attached to the stage 2.

Figure 3A:
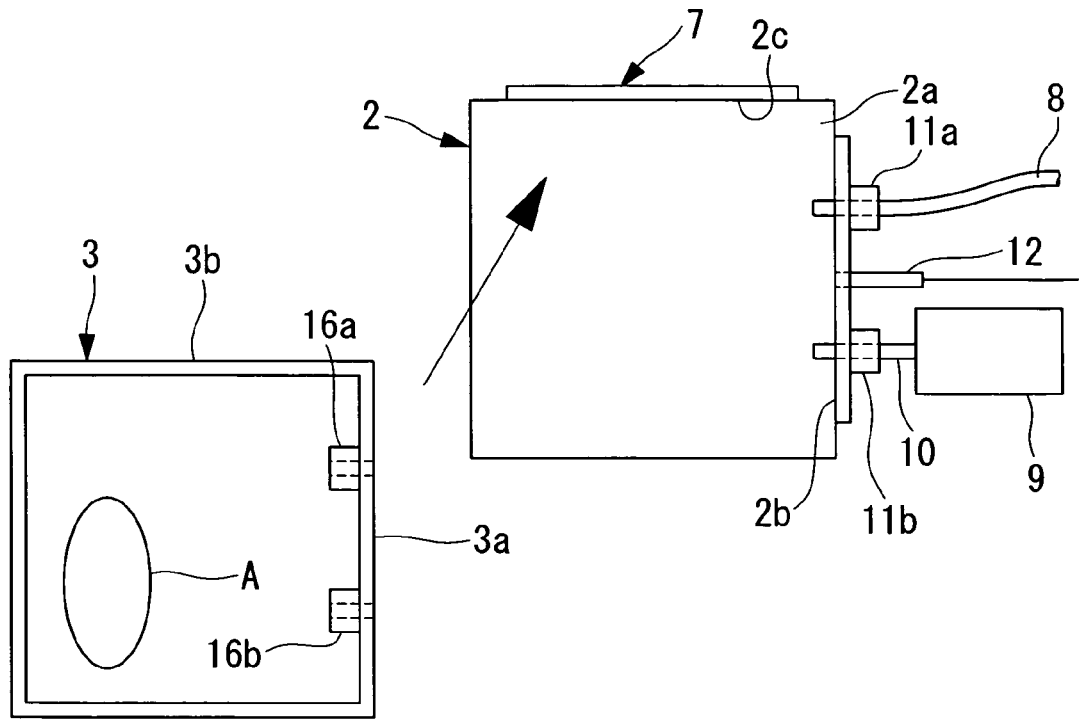
FIG. 3A is an explanatory diagram regarding a procedure for attaching the anesthetizing chamber to the stage of the in-vivo examination apparatus of FIG. 1.
Figure 3B:
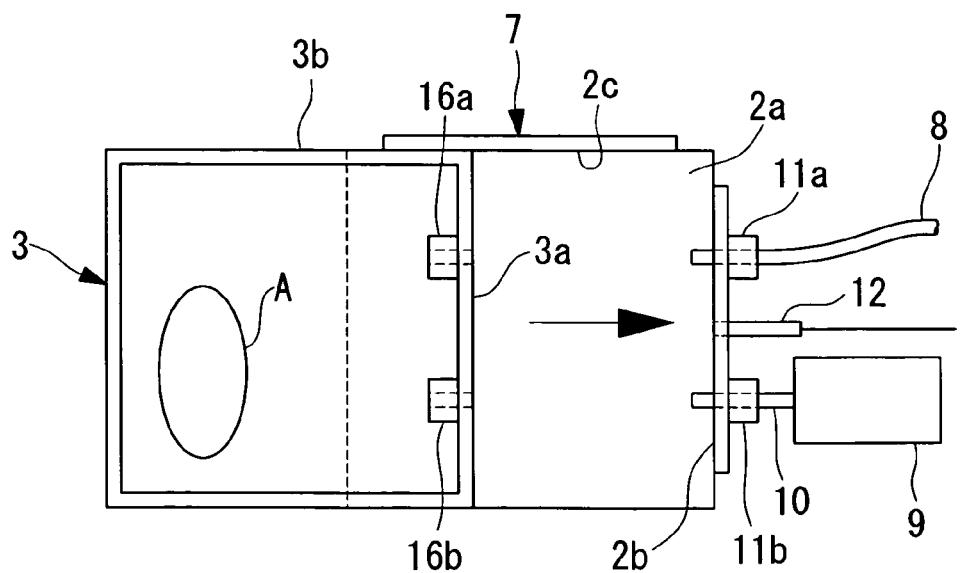
FIG. 3B is an explanatory diagram regarding the procedure for attaching the anesthetizing chamber to the stage of the in-vivo examination apparatus of FIG. 1.
Figure 3C:
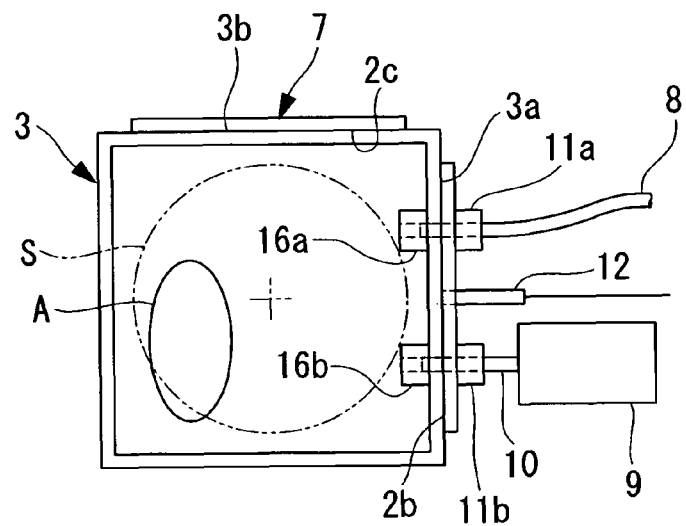
FIG. 3C is an explanatory diagram regarding the procedure for attaching the anesthetizing chamber to the stage of the in-vivo examination apparatus of FIG. 1.

The stage 2 is fixed to the base 6 in a manner such that the mounted anesthetizing chamber 3 can be moved in two horizontal directions relative to the base 6. The stage 2 is provided with a positioning mechanism 7 for fixing the anesthetizing chamber 3 in a positioned state. The positioning mechanism 7 is composed of two abutment faces 2b and 2c extending in vertical directions from the mounting face 2a of the stage 2. As shown in FIG. 3A to FIG. 3C, these abutment faces 2b and 2c are disposed in a mutually orthogonal manner, against which two adjacent side walls 3a and 3b of the rectangular anesthetizing chamber 3 are abutted so that thereby the anesthetizing chamber 3 can be positioned relative to the stage 2.

Moreover, the abutment face 2b on one side is attached with: a connector 11a for connecting a pipeline 8, which supplies anesthetic gas G from the anesthetic gas supply device 4, to the anesthetizing chamber 3; and a connector 11b for connecting a pipeline 10, which is directed to a filter 9 (refer to FIG. 3A to FIG. 3C), to the anesthetizing chamber 3. In addition, the abutment face 2b is provided with a sensor 12 for detecting that the anesthetizing chamber 3 is abutted thereagainst.

The anesthetic gas supply device 4 comprises: an anesthetic gas cylinder 13 which contains the anesthetic gas G; a vaporizer 14 which vaporizes the anesthetic gas G, sent from the anesthetic gas cylinder 13, to set at a predetermined concentration; and pipelines 8, 10, and 15 for connecting them. One ends of the pipelines 8 and 10 are connected to the connectors 11a and 11b provided to the abutment face 2b. The connector 11a connected with the pipeline 8 of the anesthetic gas supply device 4 is normally retained in a closed state, and is opened when connected to a connector 16a of the anesthetizing chamber 3 that will be described later.

In addition, to the vaporizer 14 of the anesthetic gas supply device 4 is connected a control unit 17 for controlling the operation of the vaporizer 14. Into the control unit 17, output signals from the sensor 12 of the abutment face 2b are input. The control unit 17 is designed such that; when an output signal which indicates that the anesthetizing chamber 3 has been attached, is input from the sensor 12, then the vaporizer 14 of the anesthetic gas supply device 4 is operated to vaporize the anesthetic gas G sent from the anesthetic gas cylinder 13 and to supply the vaporized gas into the anesthetizing chamber 3.

Figure 2:
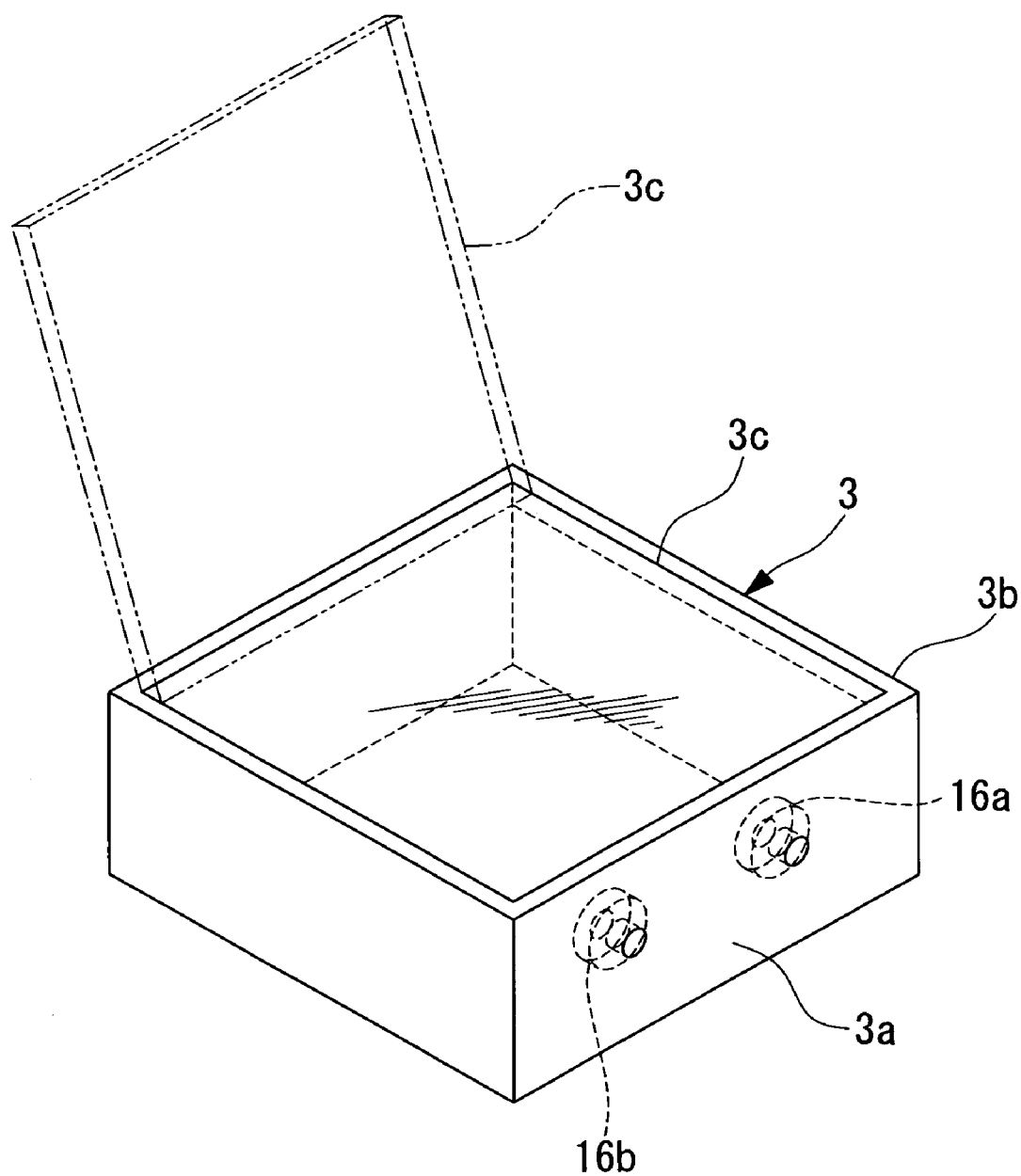
FIG. 2 is a perspective view showing the anesthetizing chamber to be provided in the in-vivo examination apparatus of FIG. 1.

As shown in FIG. 2, the anesthetizing chamber 3 is a rectangular-box-shaped member having an openable/closable transparent lid 3c, and has a sufficient content volume for accommodating the specimen A. As a result, the specimen A such as a small laboratory animal that is actively moving in an unanesthetized state can be readily housed inside the anesthetizing chamber 3.

The side wall 3a of the anesthetizing chamber 3 is provided with two connectors 16a and 16b which are to be connected to the connectors 11a and 11b provided to the positioning mechanism 7 of the stage 2. These connectors 16a and 16b are both retained in a closed state when they are not connected to the connectors 11a and 11b of the positioning mechanism 7, and are opened when connected to the connectors 11a and 11b.

As shown in FIG. 1, the observation optical system 5 comprises: an illumination system 18; a lens unit 19 for converging reflected light or fluorescent light from the specimen A due to illumination light L from the illumination system 18, to effect image formation thereof; absorbing filters 20 through which light to be used for image pickup, among the condensed light, can be exclusively passed; and an image-acquisition unit 21 such as a CCD camera for picking up the image using the light that has been passed through the absorbing filter 20.

The illumination system 18 comprises: an external illumination system 18a for irradiating the illumination light L from the outside of the lens unit 19 onto the specimen A; and an epi-illumination system 18b for making the illumination light L incident along the optical axis C of the lens unit 19 during observation at high magnification.

The lens unit 19 comprises a plurality of lens groups 24a and 24b which are attached to a turret 23. The turret 23 is supported in a horizontally rotatable manner about a support column 22 that stands from the base 6. By horizontally rotating the turret 23 about the support column 22, different lens groups 24a and 24b can be selectively arranged on the optical axis C between the stage 2 and the image-acquisition unit 21.

Each lens group 24a or 24b comprises an objective lens 25a or 25b for converging light from the specimen A, and an image-forming lens 26a or 26b for forming an image with the condensed light. The objective lenses 25a and 25b of the respective lens groups 24a and 24b have different magnifications, and the image-forming lenses 26a and 26b assembled therein are those suitable for the objective lenses 25a and 25b respectively. In addition, the lens group 24b of high magnification is provided with a zoom mechanism 27, and a dichroic mirror 28 for making the illumination light L from the epi-illumination system 18b incident along the optical axis C.

A plurality of types of absorbing filters 20 having different absorption properties are attached to a horizontally-rotatable turret 29. By rotating the turret 29, any one of the absorbing filters 20 can be selectively arranged on the optical axis C between the image-acquisition unit 21 and the lens group 24a or 24b.

Hereunder is a description of the operation of thus constituted in-vivo examination apparatus 1 according to the present embodiment.

In order to observe the specimen A such as a small laboratory animal in vivo with use of the in-vivo examination apparatus 1 according to the present embodiment, the configuration is such that: the lid 3c of the anesthetizing chamber 3 is opened; the specimen A is transferred therein; and then the lid 3c is closed.

At this time, the specimen A is unanesthetized, and thus is actively moving. However, since the anesthetizing chamber 3 has a sufficiently large content volume, the operator can readily transfer the specimen A thereinto without hustle. Moreover, since the anesthetizing chamber 3 can be detached from the stage 2, the operator can transfer the specimen A not in a narrow environment on the stage 2 but in a wider environment. As a result, the workability can be improved.

Next, the anesthetizing chamber 3 having the specimen A housed therein is attached to the stage 2.

Specifically, as shown in FIG. 3A to FIG. 3C: the anesthetizing chamber 3 is brought closer to the stage 2 in a horizontal direction; then, (a) the side wall 3b on one side of the anesthetizing chamber 3 is abutted against the abutment face 2c which is not provided with the connectors 11a and 11b; (b) in the state of (a), the side wall 3b of the anesthetizing chamber 3 is slidingly moved relative to the abutment face 2c; and (c) the connectors 16a and 16b of the anesthetizing chamber 3 are simultaneously inserted into the connectors 11a and 11b provided to the other abutment face 2b. As a result, the pipeline 8 and the pipeline 10 from the anesthetic gas supply device 4 and the filter 9 are connected to the anesthetizing chamber 3.

By so doing, the anesthetizing chamber 3 is fixed to the stage 2 in a positioned state. In addition, the pipelines 8 and 10 are opened to the anesthetizing chamber 3 at the time when the connectors 11a/16a and the connectors 11b/16b are respectively connected.

At this time, the sensor 12 provided to the abutment face 2b detects the attachment of the anesthetizing chamber 3, and outputs a detection signal. The detection signal from the sensor 12 is sent to the control unit 17, and the control unit 17 actuates the vaporizer 14.

Accordingly, the anesthetic gas G sealed in the anesthetic gas cylinder 13 is vaporized, and the gas G in a vaporized state is sent to the anesthetizing chamber 3 through the pipeline 8 and fills the anesthetizing chamber 3. As a result, the specimen A housed inside the anesthetizing chamber 3 can be anesthetized to be placed in an anesthetized state. Since the space in the anesthetizing chamber 3 is also opened to the pipeline 10 connected to the filter 9, the concentration of the anesthetic gas G in the anesthetizing chamber 3 can be kept constant by discharging the anesthetic gas G from the anesthetizing chamber 3 through the filter 9.

By so doing, the specimen A inside the anesthetizing chamber 3 falls in an anesthetized state at an optional position in the anesthetizing chamber 3.

Here, in order to observe the specimen A in an anesthetized state in this manner, firstly, the turret 23 is rotated to select a low magnification lens group 24a having a visual field S which covers approximately the whole anesthetizing chamber 3. As a result, the illumination light L emitted from the external illumination system 18a is irradiated to the whole anesthetizing chamber 3 on the stage 2. Then, the reflected light from the specimen A etc. is converged by the objective lens 25a, and the image-forming lens 26a forms an image using the light. The image is then captured by the image-acquisition unit 21 through the absorbing filter 20.

Figure 4A:
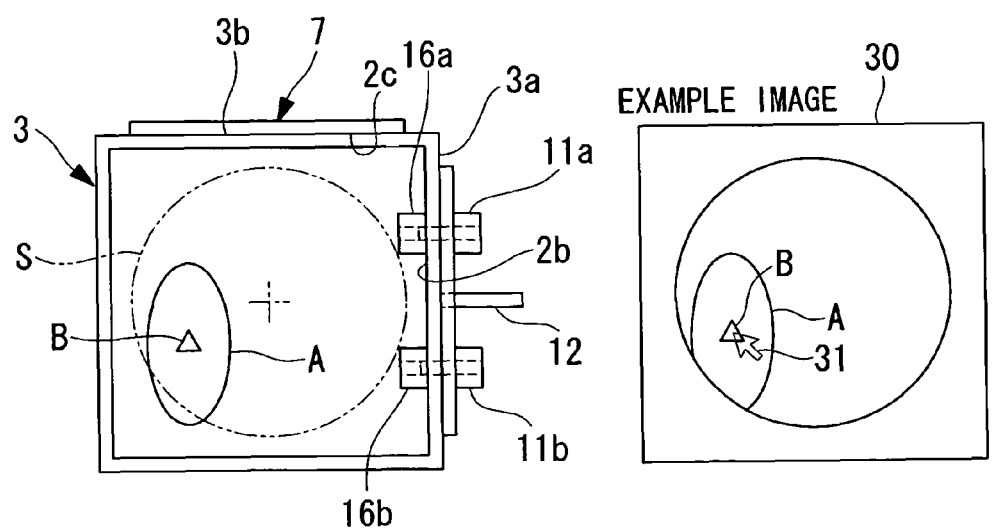
FIG. 4A shows a procedure for observing a specimen inside the anesthetizing chamber that has been attached by the procedure of FIG. 3A to FIG. 3C.
Figure 4B:
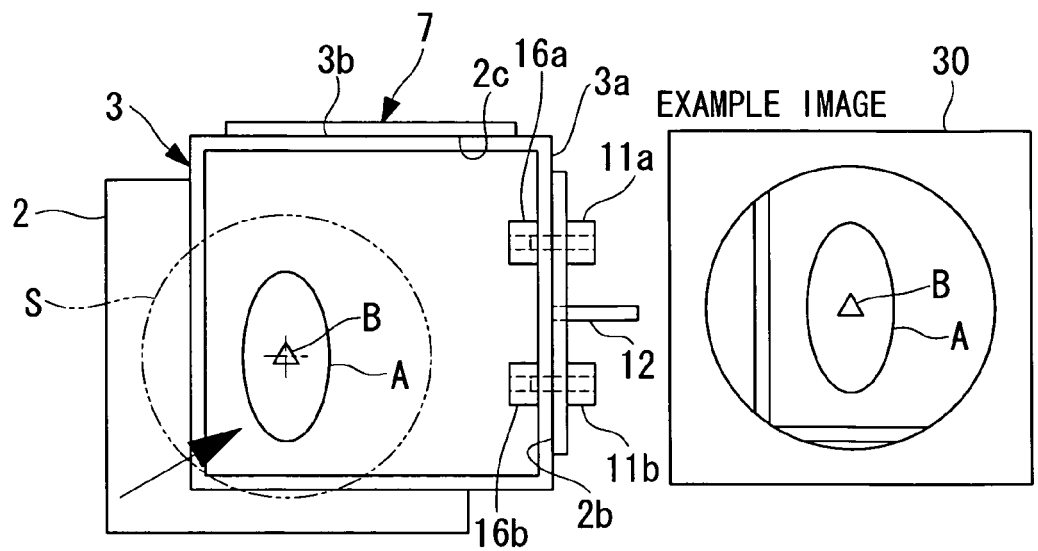
FIG. 4B shows the procedure for observing the specimen inside the anesthetizing chamber that has been attached by the procedure of FIG. 3A to FIG. 3C.

For example, as shown in FIG. 4A, even in a case where the specimen A falls in an anesthetized state in a corner of the anesthetizing chamber 3, at least a part of the specimen A can be displayed on the monitor 30 by selecting the low magnification lens group 24a. The operator specifies the specimen A to be observed by placing the cursor 31 thereon in the monitor 30, with use of an input device (not shown) such as a mouse. As a result, the stage 2 can be operated so that, as shown in FIG. 4B, the specified position is located in the center of the visual field S, and the specimen A to be observed can be located in the central position of the monitor 30.

Figure 4C:
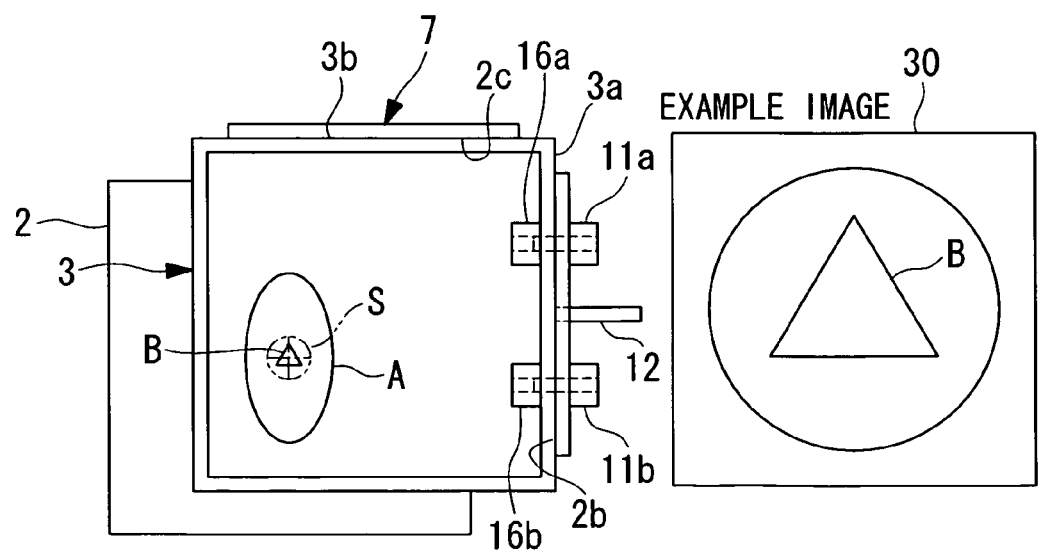
FIG. 4C shows the procedure for observing the specimen inside the anesthetizing chamber that has been attached by the procedure of FIG. 3A to FIG. 3C.

In this state, the turret 23 is rotated to select the high magnification lens group 24b. Then, the epi-illumination system 18b is operated to make the illumination light L incident along the optical axis C of the lens group 24b via the dichroic mirror 28. As a result, high intensity illumination light L is irradiated on the specified position of the specimen A, and, as shown in FIG. 4C, an enlarged image of the part of interest B of the specimen A is displayed on the monitor 30 by the high magnification lens group 24b.

In this way, in the in-vivo examination apparatus 1 according to this embodiment, since the anesthetizing chamber 3 for housing the specimen A is detachably attached to the stage 2, the operation for transferring the specimen A can be readily performed in a wide environment.

Moreover, since the configuration is such that: the anesthetizing chamber 3 is connected to the anesthetic gas supply device 4 through the attachment to the stage 2; and the vaporizer 14 is actuated through the operation of the sensor 12; therefore, the anesthetic gas G supplied from the anesthetic gas cylinder 13 can be supplied into the anesthetizing chamber 3 without leakage. Accordingly, it is made possible to prevent leakage of the anesthetic gas G while continuously supplying an appropriate concentration of the anesthetic gas G, so that the specimen A can be maintained in an anesthetized state over a long period of time. As a result, observation of the specimen A in vivo can be readily performed.

In the description of this embodiment, the configuration is such that the anesthetizing chamber 3 is mounted on the stage 2 before the specimen A is anesthetized; however, instead of this, the configuration may also be such that the specimen A is previously anesthetized before the anesthetizing chamber 3 is mounted on the stage 2. Specifically, since the anesthetizing chamber 3 is provided with the connectors 16a and 16b to be connected to the anesthetic gas supply device 4, the specimen A can be anesthetized before being mounted on the stage 2 by connecting the anesthetizing chamber 3 to a preliminary anesthetizing device (not shown) which has connectors in common with the connectors 11a and 11b of the anesthetic gas supply device 4, if such a preliminary anesthetizing device has been prepared.

Moreover, a plurality of specimens A may also be housed in the anesthetizing chamber 3; in which case, the configuration may also be such that the inside of the anesthetizing chamber 3 is partitioned into a plurality of housing spaces by partition walls so that the specimens A can be individually housed therein.

The invention claimed is:

1. An in-vivo examination apparatus comprising:
   a stage configured to move in at least two directions for mounting a specimen such as a laboratory animal;
   an anesthetizing chamber which is detachably disposed on the stage for housing the specimen;
   a positioning device that is provided in the stage, for fixing the anesthetizing chamber to the stage, in a positioned state by abutting the anesthetizing chamber;
   an anesthetic gas supply device for supplying anesthetic gas into the anesthetizing chamber; and
   a connecting mechanism for connecting said anesthetic gas supply device and the anesthetizing chamber via the positioning device when the anesthetizing chamber is attached to the stage;
   wherein a transparent window is provided on at least a part of the anesthetizing chamber.

2. An in-vivo examination apparatus comprising:
a stage for mounting a specimen such as a laboratory animal;
an anesthetizing chamber which is disposed on the stage for housing the specimen;
an anesthetic gas supply device for supplying anesthetic gas into the anesthetizing chamber; and
a sensor for detecting the attachment/detachment of the anesthetizing chamber to/from said stage; and a control unit for operating said anesthetic gas supply device on the basis of a detection signal from the sensor which indicates the attachment of the anesthetizing chamber to the stage;
wherein a transparent window is provided on at least a part of the anesthetizing chamber.

* * * * *